United States Patent
Kita et al.

(10) Patent No.: US 8,680,325 B2
(45) Date of Patent: Mar. 25, 2014

(54) PROCESS FOR PREPARING 2,5-DIHYDROXYTEREPHTHALIC ACID

(75) Inventors: Yusuke Kita, Osaka (JP); Ryoichi Otsuka, Osaka (JP)

(73) Assignee: Ueno Fine Chemicals Industry, Ltd., Osaka (JP)

( * ) Notice: Subject to any disclaimer, the term of this patent is extended or adjusted under 35 U.S.C. 154(b) by 98 days.

(21) Appl. No.: 13/482,241

(22) Filed: May 29, 2012

(65) Prior Publication Data

US 2012/0310008 A1  Dec. 6, 2012

(30) Foreign Application Priority Data

May 30, 2011 (JP) ................................. 2011-120548
Feb. 3, 2012 (JP) ................................. 2012-022050

(51) Int. Cl.
*C07C 51/15* (2006.01)

(52) U.S. Cl.
USPC ........................... 562/424; 562/405; 562/423

(58) Field of Classification Search
None
See application file for complete search history.

(56) References Cited

U.S. PATENT DOCUMENTS 6,040,478 A * 3/2000 Sikkema et al. ............... 562/424

FOREIGN PATENT DOCUMENTS

| GB | 1108023 | | 3/1968 |
| JP | 49-11841 | A | 2/1974 |
| JP | 11-515031 | A | 12/1999 |
| JP | 2011-26232 | A | 2/2011 |
| WO | 97/17315 | A1 | 5/1997 |

OTHER PUBLICATIONS

Extended European Search Report for Application No. 12169471.5 dated Oct. 8, 2012.

* cited by examiner

*Primary Examiner* — Patrick Lewis
(74) *Attorney, Agent, or Firm* — Sughrue Mion, PLLC

(57) ABSTRACT

The present invention provides a process for preparing 2,5-dihydroxyterephthalic acid which comprises reacting a dialkali metal salt of hydroquinone with carbon dioxide in a reaction medium in the presence of a potassium salt represented by formula (I):

$$C_nH_{2n+1}COOK \qquad (I)$$

wherein n is an integer of 1-17.

According to the process for preparing 2,5-dihydroxyterephthalic acid of the present invention, 2,5-dihydroxyterephthalic acid can be produced both safely and at a low cost under industrially advantageous conditions. Further, the process according to the present invention causes less damage to reaction equipment and the like.

6 Claims, No Drawings

PROCESS FOR PREPARING 2,5-DIHYDROXYTEREPHTHALIC ACID

TECHNICAL FIELD

The present invention relates to a process for preparing 2,5-dihydroxyterephthalic acid which comprises reacting a dialkali metal salt of hydroquinone with carbon dioxide.

BACKGROUND ART 2,5-dihydroxyterephthalic acid (2,5-dihydroxyterephthalic acid may be also referred to as DHTA hereinafter) is an aromatic dicarboxylic acid having two hydroxyl groups. DHTA is useful as a monomer for manufacturing synthetic resins such as polyesters, polyamides, aramids and the like and as a raw material for synthesizing fluorescent agents, intermediates of medicines and the like. Therefore, the demand for DHTA is growing year by year.

A conventionally known process for introducing carboxyl group(s) into a compound having phenolic hydroxyl group(s) is the Kolbe-Schmitt reaction. Examples of the Kolbe-Schmitt reactions include a chemical reaction which comprises contacting an alkaline metal phenoxide (an alkali metal salt of phenol) with carbon dioxide at a high temperature under a high pressure to carboxylate the ortho position of the alkaline metal phenoxide and neutralizing the resulting compound with an acid to give salicylic acid.

With regard to processes for the preparation of DHTA, Patent document 1 (Japanese Patent Application Laid Open No. Sho 49-11841) discloses a process for preparing DHTA by using the Kolbe-Schmitt reaction. However, in this process, the dicarboxylation reaction of hydroquinone to provide DHTA requires a very high pressure. Further, according to this process, DHTA can only be produced with a low conversion ratio and in a low yield.

As a process for introducing carboxyl group(s) under relatively mild conditions, Patent document 2 (Japanese Patent Application Laid Open No. Hei 11-515031 corresponding to WO 97/17315) discloses a process which comprises contacting a dihydric phenol with carbon dioxide in the presence of an alkali metal carbonate and of an alkali metal formate at a temperature above the melting point of the formate.

According to the process disclosed in Patent document 2, DHTA can be obtained in a relatively high yield, but the process requires a large amount of an expensive alkali metal formate. Further, the process involves generation of carbon monoxide. Therefore, the process is not industrially advantageous in terms of safety. Furthermore, this process has a problem of insufficient stirring because a large amount of the alkaline metal formate becomes solidified when the reaction system is cooled after the completion of the reaction. Additionally, this process has another problem of damaging stirring machines and the like because the contents of the reaction system after the completion of the reaction tend to strongly adhere to the reaction equipment.

In order to improve the process disclosed in Patent document 2, Patent document 3 (Japanese Patent Application Laid Open No. 2011-26232) discloses a process for preparing DHTA which comprises a dicarboxylation reaction followed by treatment with a mineral acid. However, this process also requires the use of an expensive alkaline metal formate and cannot solve the problems of the process disclosed in Patent document 2. Therefore, this process is not sufficiently advantageous.

[Patent document 1] Japanese Patent Application Laid Open No. Sho 49-11841
[Patent document 2] Japanese Patent Application Laid Open No. Hei 11-515031 (corresponding to WO 97/17315)
[Patent document 3] Japanese Patent Application Laid Open No. 2011-26232

SUMMARY OF THE INVENTION

Problem to be Solved by the Invention

An object of the present invention is to provide a process for preparing DHTA under industrially advantageous conditions both safely and at a low cost.

Another object of the present invention is to provide a process for preparing DHTA which causes less damage to reaction equipment and the like.

Means for Solving the Problem

The present inventors conducted studies on processes for reacting dialkali metal salts of hydroquinone with carbon dioxide in reaction media. As a result, the present inventors have found that a process which comprises reacting a dialkali metal salt of hydroquinone with carbon dioxide in the presence of a certain type of potassium salt makes it possible for the reaction to progress under relatively mild conditions and makes it possible to provide DHTA in a high yield.

The present invention provides a process for preparing 2,5-dihydroxyterephthalic acid which comprises reacting a dialkali metal salt of hydroquinone with carbon dioxide in a reaction medium in the presence of a potassium salt represented by formula (I):

$$C_nH_{2n+1}COOK \qquad (I)$$

wherein n is an integer of 1-17.

The Effect of the Invention Superior to the Conventional Art

According to the present invention, DHTA can be produced safely at a low cost under conditions of relatively low temperatures and low pressures in a high yield. Further, the process according to the present invention causes less damage to reaction equipment and the like.

DETAILED DESCRIPTION OF THE PREFERRED EMBODIMENTS

In the process for preparing 2,5-dihydroxyterephthalic acid according to the present invention, the so-called Kolbe-Schmitt reaction is used for reacting the dialkali metal salt of hydroquinone with carbon dioxide. In the process according to the present invention, the reaction is generally carried out under stirring.

The reaction apparatus used in the process according to the present invention is not limited and may be an apparatus commonly used in the Kolbe-Schmitt reaction. Preferable examples of the reaction apparatuses include an autoclave resistant to a high pressure reaction and equipped with a stirring machine. More preferable examples of the reaction apparatuses include an apparatus which has a temperature control function and is equipped with an introduction pipe for introducing gasses such as carbon dioxide, inert gasses and the like, a clamp for supporting a thermometer, a pressure gauge, an exhaust pipe and the like.

Examples of the dialkali metal salt of hydroquinone used for the process according to the present invention include dilithium salt of hydroquinone, disodium salt of hydroquinone, dipotassium salt of hydroquinone, dirubidium salt of hydroquinone and dicesium salt of hydroquinone. Among them, disodium salt of hydroquinone and dipotassium salt of hydroquinone are preferable in terms of availability, cost and reactivity, and dipotassium salt of hydroquinone is more preferable in terms of its higher reactivity.

The dialkali metal salt of hydroquinone can be obtained by converting hydroquinone to its dialkali metal salt by using an alkali metal hydroxide or an alkali metal alkoxide such as an alkali metal t-butoxide, an alkali metal methoxide, an alkali metal ethoxide and an alkali metal i-propoxide. In terms of cost, it is especially preferable to convert hydroquinone to its dialkali metal salt by using an alkali metal hydroxide.

Dipotassium salt of hydroquinone can be obtained by converting hydroquinone to its dipotassium salt by using potassium hydroxide or a potassium alkoxide such as potassium t-butoxide, potassium methoxide, potassium ethoxide and potassium i-propoxide. In terms of cost, it is especially preferable to convert hydroquinone to its dipotassium salt by using potassium hydroxide.

As with dipotassium salt of hydroquinone, disodium salt of hydroquinone can be obtained by converting hydroquinone to its disodium salt by using sodium hydroxide or a sodium alkoxide such as sodium t-butoxide, sodium methoxide, sodium ethoxide and sodium i-propoxide. In terms of cost, it is especially preferable to convert hydroquinone to its disodium salt by using sodium hydroxide.

It is required that the dialkali metal salt of hydroquinone subjected to the reaction be sufficiently dehydrated. If the dehydration is insufficient, the reaction yield tends to decrease. The dehydration is carried out by heating the dialkali metal salt of hydroquinone in a vacuum, for example, with an apparatus such as an evaporator. The dehydration is carried out until the water content is preferably equal to or less than 1% by weight, more preferably equal to or less than 0.5% by weight and the most preferably equal to or less than 0.3% by weight.

In the process according to the present invention, the reaction of the dialkali metal salt of hydroquinone with carbon dioxide is carried out in the presence of the potassium salt represented by formula (I):

$$C_nH_{2n+1}COOK \qquad (I)$$

wherein n is an integer of 1-17.

Methods for obtaining the potassium salt represented by formula (I) are not especially limited. For example, a commercially available potassium salt represented by formula (I) may be used. Alternatively, the potassium salt represented by formula (I) may be prepared by converting a saturated carboxylic acid ($C_nH_{2n+1}COOH$) to its potassium salt by using potassium hydroxide or the like.

By using the potassium salt represented by formula (I), a dialkali metal salt of DHTA can be prepared at a relatively low temperature of around 150-290° C. in a high yield. By subjecting the resulting dialkali metal salt of DHTA to a conventionally used means for converting a salt to its acid, such as precipitation with an acid, DHTA, which is the objective compound, can be obtained in a high yield.

Additionally, since the potassium salt represented by formula (I) need not be melted during the reaction, the potassium salt does not solidify even in the cooling step after the completion of the reaction. Therefore, aftertreatment steps can be easily performed and damage to the reaction apparatus can be prevented.

The amount of the potassium salt represented by formula (I) used for the process according to the present invention is preferably 0.1-10 parts by mole, more preferably 0.3-5 parts by mole, even more preferably 0.5-4.5 parts by mole and the most preferably 1-3 parts by mole per one part by mole of the dialkali metal salt of hydroquinone.

If the amount of the potassium salt represented by formula (I) added to one part by mole of the dialkali metal salt of hydroquinone is less than 0.1 parts by mole, the reaction tends not to proceed sufficiently. On the other hand, if the amount of the potassium salt represented by formula (I) added to one part by mole of the dialkali metal salt of hydroquinone is more than 10 parts by mole, the yield tends to have peaked, and therefore, the process tends to be unfavorable in terms of cost.

Preferable examples of the potassium salt represented by formula (I) used in the process of the present invention include potassium acetate, potassium isobutyrate, potassium palmitate, potassium stearate and combinations thereof. In particular, potassium acetate is more preferably used because of high reaction yields.

Among the above potassium salt represented by formula (I), any one kind of the potassium salt may be used alone, or alternatively, any combination of two or more kinds of the potassium salt may be used.

In the process of the present invention, the reaction medium used for the reaction of the dialkali metal salt of hydroquinone with carbon dioxide is that which exists as a liquid at the reaction temperature under the reaction pressure and which is inert to the reaction of the dialkali metal salt of hydroquinone with carbon dioxide. Preferably, the reaction medium is that which has a boiling point equal to or higher than 220° C. under atmospheric pressure.

Preferable examples of the reaction media used for the process according to the present invention include aliphatic, alicyclic and aromatic hydrocarbons as well as ether compounds having these hydrocarbon groups. In more detail, examples of the reaction media include light oil, kerosene, lubricating oil, white oil, alkyl benzene, alkyl naphthalene, triphenyl hydride, diphenyl ether, alkyl phenyl ether, alkyl diphenyl ether, higher alcohols having high boiling points such as isooctyl alcohol and mixtures thereof.

The amount of the reaction medium used for the process according to the present invention is preferably equal to or more than 0.5, more preferably 1-15 and the most preferably 6-12 times the amount of the dialkali metal salt of hydroquinone by weight.

The temperature of the reaction of the dialkali metal salt of hydroquinone with carbon dioxide is relatively low owing to the presence of the potassium salt represented by formula (I). The reaction temperature is preferably 150-290° C., more preferably 200-285° C., and the most preferably 230-280° C. If the reaction temperature is lower than 150° C., the reaction tends not to proceed well. On the other hand, if the reaction temperature is higher than 290° C., the yield tends to have peaked, and therefore, the process tends to be unfavorable owing to loss of energy. Further, at such a high reaction temperature, side-reactions may occur.

The pressure of the reaction of the dialkali metal salt of hydroquinone with carbon dioxide is preferably a carbon dioxide pressure of 0-10 MPa, and more preferably a carbon dioxide pressure of 0-5 MPa.

The reaction time may be adjusted depending on other conditions, and is preferably from a few minutes to 15 hours, more preferably from 10 minutes to 10 hours, even more preferably from 20 minutes to 10 hours and the most preferably from 1 to 5 hours.

According to the process of the present invention, the dialkali metal salt of DHTA can be prepared at a relatively low temperature under a relatively low pressure in a high yield. By subjecting the resulting dialkali metal salt of DHTA to a conventionally used means for converting a salt to its acid, such as precipitation with an acid, DHTA, which is the objective compound, can be obtained in a high yield.

The present invention is further described in detail by the following examples. The examples are intended to illustrate the invention and are not to be construed as limiting the scope of the invention.

EXAMPLES

Example 1

4.5 g (24.2 mmoles) of dipotassium salt of hydroquinone, 4.75 g (48.4 mmoles) of potassium acetate and 45 g of light oil were fed into a 120 mL autoclave. After the closing of the autoclave, the air was displaced by nitrogen. Under the nitrogen atmosphere, stirring commenced.

Then, the mixture was heated to 250° C. and the nitrogen was replaced with carbon dioxide. The reaction was carried out under a carbon dioxide pressure of 0.9 MPa with stirring for 3 hours. After the reaction was completed, the reaction mixture was cooled (to <100° C.). After the opening of the autoclave, 30 g of hydrochloric acid (5.90% by weight) was added thereto. The autoclave was then closed and nitrogen was introduced into the autoclave. Under the nitrogen atmosphere, stirring was carried out for 15 minutes.

Thereafter, the precipitate obtained after precipitation with hydrochloric acid was collected by suction filtration and then dissolved in about 360 g of methanol. The filtrate was heated to 60-70° C. with stirring, then was separated into the aqueous and reaction medium layers, both of which were collected.

The resultant methanol solution, the aqueous layer and the reaction medium layer were subjected to quantitative analysis by means of high-performance liquid chromatography. As a result, conversion ratios from the fed amount of dipotassium salt of hydroquinone were: benzoquinone 0.01%; 2,5-dihydroxybenzoic acid 6.92%; 2,5-dihydroxyterephthalic acid 86.39%; the remainder being unreacted hydroquinone 5.83%. The concentration of carbon monoxide determined on completion of the reaction was 46 ppm. The result is shown in Table 1. As described above, after the reaction was completed, the reaction mixture was cooled. The content of the reaction system obtained after the cooling was a slurry, which could be easily removed from the reaction system.

Comparative Example 1

The reaction was carried out in the same manner as described in Example 1 except that potassium acetate was not fed into the autoclave. As a result, conversion ratios from the fed amount of dipotassium salt of hydroquinone were: benzoquinone 0.05%; 2,5-dihydroxybenzoic acid 1.77%; 2,5-dihydroxyterephthalic acid 3.07%; the remainder being unreacted hydroquinone 92.37%. The result is shown in Table 1.

Examples 2-4

The reactions were carried out in the same manner as described in Example 1 except that dipotassium salt of hydroquinone and the potassium salts represented by formula (I) were used at molar ratios shown in Table 1. The results are shown in Table 1. The contents of the reaction systems obtained after the completion of the reactions were slurries or pastes, which could be easily removed from the reaction systems.

Comparative Example 2

The reaction was carried out in the same manner as described in Example 1 except that 4.07 g (48.4 mmoles) of potassium formate instead of potassium acetate was fed into the autoclave. The result is shown in Table 1. The concentration of carbon monoxide determined on the completion of the reaction was above 500 ppm (the limit value). The content of the reaction system obtained after the completion of the reaction strongly adhered to the bottom of the autoclave and could not be easily removed from the reaction system. Further, the content damaged the stirring machine and the like.

TABLE 1

| | potassium salt | molar ratio | conversion ratio (%) | | | | | CO concentration (ppm) |
| --- | --- | --- | --- | --- | --- | --- | --- | --- |
| | | | HQ | BQ | DHBA | DHTA | unknown products | |
| Example 1 | $CH_3COOK$ | 2.0 | 5.83 | 0.01 | 6.92 | 86.39 | 0.85 | 46 |
| Comparative Example 1 | — | 0 | 92.37 | 0.05 | 1.77 | 3.07 | 2.74 | — |
| Example 2 | $i\text{-}C_3H_7COOK$ | 2.0 | 11.35 | N.D. | 7.93 | 78.15 | 2.57 | 48 |
| Example 3 | $C_{15}H_{31}COOK$ | 0.5 | 0.67 | N.D. | 6.55 | 70.17 | 22.61 | 45 |
| Example 4 | $C_{17}H_{35}COOK$ | 0.5 | 6.55 | 0.02 | 4.87 | 45.89 | 42.67 | 48 |
| Comparative Example 2 | HCOOK | 2.0 | 11.73 | N.D. | 4.13 | 83.48 | 0.66 | ≧500 |

HQ: hydroquinone
BQ: benzoquinone
DHBA: 2,5-dihydroxybenzoic acid
DHTA: 2,5-dihydroxyterephthalic acid
Molar ratio: ratio of molar amount of the potassium salt to molar amount of dipotassium salt of hydroquinone

Example 5

The reaction was carried out in the same manner as described in Example 1 except that 4 g (26.0 mmoles) of disodium salt of hydroquinone were used instead of dipotassium salt of hydroquinone and that the fed amount of potassium acetate was changed to 5.1 g (51.9 mmoles).

As a result, conversion ratios from the fed amount of disodium salt of hydroquinone were: benzoquinone 0.01%; 2,5-dihydroxybenzoic acid 7.70%; 2,5-dihydroxyterephthalic acid 79.83%; the reminders being unreacted hydroquinone 9.10% and unknown products 3.36%. As described above, after the reaction was completed, the reaction mixture was cooled. The content of the reaction system obtained after the cooling was a slurry, which could be easily removed from the reaction system.

Examples 6-9

The reactions were carried out in the same manner as described in Example 1 except that potassium acetate was used at molar ratios shown in Table 2. The results are shown in Table 2.

TABLE 2

| | molar ratio | conversion ratio (%) | | | | |
| --- | --- | --- | --- | --- | --- | --- |
| | | HQ | BQ | DHBA | DHTA | unknown products |
| Example 6 | 0.47 | 70.62 | 0.05 | 2.13 | 23.32 | 3.88 |
| Example 7 | 1.0 | 43.27 | 0.01 | 5.47 | 47.53 | 3.72 |
| Example 8 | 1.5 | 31.67 | 0.01 | 7.15 | 57.98 | 3.19 |
| Example 9 | 2.5 | 11.39 | 0.01 | 5.96 | 79.58 | 3.06 |

Example 10

4.74 g (25.4 mmoles) of dipotassium salt of hydroquinone, 4.98 g (50.7 mmoles) of potassium acetate and 47.4 g of light oil were fed into a 200 mL four neck flask. After closing the flask, nitrogen was introduced into the flask at a ratio of about 100 mL/min. Under this condition, the reaction system was kept stirred.

Then, the mixture was heated to 250° C., and the nitrogen was replaced with carbon dioxide. The reaction was carried out for 3 hours with stirring. After the reaction was completed, the reaction mixture was cooled (to <100° C.). After the opening of the flask, 30 g of hydrochloric acid (12.4% by weight) was added thereto. The flask was then closed and nitrogen was introduced into the flask. Under the nitrogen atmosphere, stirring was carried out for 15 minutes. All the steps and analyses that followed were carried out in the same manner as described in Example 1. The result is shown in Table 3.

Examples 11-14

The reactions were carried out in the same manner as described in Example 1 except that reaction pressures were changed to the pressures shown in Table 3. The results are shown in Table 3.

TABLE 3

| | reaction pressure (MPa) | conversion ratio (%) | | | | |
| --- | --- | --- | --- | --- | --- | --- |
| | | HQ | BQ | DHBA | DHTA | unknown products |
| Example 10 | 0 | 38.90 | 0.11 | 6.89 | 50.43 | 3.67 |
| Example 11 | 0.2 | 6.91 | N.D. | 7.60 | 81.66 | 3.83 |
| Example 12 | 0.3 | 9.54 | 0.01 | 7.26 | 81.02 | 2.17 |
| Example 13 | 0.6 | 8.93 | 0.07 | 6.40 | 80.14 | 4.46 |
| Example 14 | 5.0 | 2.41 | 0.01 | 4.89 | 89.21 | 3.48 |

Examples 15-19

The reactions were carried out in the same manner as described in Example 1 except that the reaction pressure was changed to 0.3 MPa and reaction temperatures were changed to temperatures shown in Table 4. The results are shown in Table 4.

TABLE 4

| | temperature (° C.) | conversion ratio (%) | | | | |
| --- | --- | --- | --- | --- | --- | --- |
| | | HQ | BQ | DHBA | DHTA | unknown products |
| Example 15 | 220 | 23.74 | 0.01 | 50.36 | 22.78 | 3.11 |
| Example 16 | 240 | 21.80 | 0.05 | 9.34 | 63.05 | 5.76 |
| Example 17 | 260 | 3.15 | 0.19 | 6.16 | 83.24 | 7.26 |
| Example 18 | 270 | 5.50 | 0.01 | 4.62 | 76.99 | 12.88 |
| Example 19 | 280 | 5.28 | N.D. | 4.35 | 78.47 | 11.90 |

Examples 20-22

The reactions were carried out in the same manner as described in Example 1 except that the reaction pressure was changed to 0.3 MPa and the reaction times were changed to reaction times shown in Table 5. The results are shown in Table 5.

TABLE 5

| | reaction time (h) | conversion ratio (%) | | | | |
| --- | --- | --- | --- | --- | --- | --- |
| | | HQ | BQ | DHBA | DHTA | unknown products |
| Example 20 | 1 | 31.44 | 0.52 | 8.42 | 55.37 | 4.25 |
| Example 21 | 2 | 15.85 | 0.18 | 7.95 | 70.57 | 5.45 |
| Example 22 | 5 | 4.63 | 0.05 | 5.75 | 83.13 | 6.44 |

What is claimed is:

1. A process for preparing 2,5-dihydroxyterephthalic acid which comprises reacting a dialkali metal salt of hydroquinone with carbon dioxide in a reaction medium in the presence of a potassium salt represented by formula (I):

$$C_nH_{2n+1}COOK \qquad (I)$$

wherein n is an integer of 1-17.

2. The process according to claim 1, wherein the dialkali metal salt of hydroquinone is dipotassium salt of hydroquinone or disodium salt of hydroquinone.

3. The process according to claim 1, wherein the dialkali metal salt of hydroquinone is reacted with carbon dioxide in the presence of 0.1-10 parts by mole of the potassium salt represented by formula (I) defined in claim per one part by mole of the dialkali metal salt of hydroquinone.

4. The process according to claim 1, wherein the potassium salt represented by formula (I) defined in claim 1 is selected from the group consisting of potassium acetate, potassium isobutyrate, potassium palmitate, potassium stearate and a combination thereof.

5. The process according to claim 1, wherein the dialkali metal salt of hydroquinone is reacted with carbon dioxide under a carbon dioxide pressure of 0-10 MPa at a temperature of 150-290° C.

6. The process according to claim 1, wherein the reaction medium is selected from the group consisting of light oil, kerosene, lubricating oil, white oil, alkyl benzene, alkyl naphthalene, triphenyl hydride, diphenyl ether, alkyl phenyl ether, alkyl diphenyl ether, isooctyl alcohol and a mixture thereof.

* * * * *